(12) United States Patent
Spindler et al.

(10) Patent No.: US 11,191,634 B2
(45) Date of Patent: Dec. 7, 2021

(54) AORTIC STENT GRAFT WITH DURABLE SUTURE ATTACHMENT SITES

(71) Applicant: Cook Medical Technologies LLC, Bloomington, IN (US)

(72) Inventors: Ralf Spindler, Solsberry, IN (US); Davorin Skender, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 124 days.

(21) Appl. No.: 16/677,125

(22) Filed: Nov. 7, 2019

(65) Prior Publication Data

US 2021/0137670 A1    May 13, 2021

(51) Int. Cl.
*A61F 2/07* (2013.01)
*A61F 2/90* (2013.01)
*D02G 3/38* (2006.01)

(52) U.S. Cl.
CPC ............ *A61F 2/07* (2013.01); *A61F 2/90* (2013.01); *D02G 3/38* (2013.01); *A61F 2002/075* (2013.01)

(58) Field of Classification Search
CPC ...... A61F 2/07; A61F 2/06; A61F 2/04; A61F 2/90; A61F 2002/075; D02G 3/38
See application file for complete search history.

(56) References Cited

U.S. PATENT DOCUMENTS

| 7,175,652 | B2 | 2/2007 | Cook et al. |
| 8,123,884 | B2 | 2/2012 | Kujawski et al. |
| 8,897,892 | B2 | 11/2014 | Fuhs et al. |
| 9,107,743 | B2 | 8/2015 | Iancea et al. |
| 2002/0052660 | A1 | 5/2002 | Greenlaugh |
| 2005/0228474 | A1 | 10/2005 | Laguna |
| 2005/0273155 | A1* | 12/2005 | Bahler ............... A61F 2/07 623/1.13 |
| 2007/0207186 | A1 | 9/2007 | Scanlon et al. |
| 2008/0319530 | A1 | 12/2008 | Leewood et al. |
| 2009/0210047 | A1 | 8/2009 | Amplatz et al. |
| 2011/0315305 | A1* | 12/2011 | Edwin ............... B29C 65/48 156/191 |
| 2012/0239134 | A1 | 9/2012 | Dierking |
| 2018/0193177 | A1 | 7/2018 | Burkart et al. |
| 2019/0167408 | A1 | 6/2019 | Harris et al. |

FOREIGN PATENT DOCUMENTS

WO    2017218474    12/2017

OTHER PUBLICATIONS

European Patent Office, Extended European Search Report for 202000B05.8-1113, dated Mar. 9, 2021, 7 pages, EPO, The Hague.

* cited by examiner

*Primary Examiner* — Dinah Baria
(74) *Attorney, Agent, or Firm* — Liell & McNeil

(57) ABSTRACT

An aortic stent graft includes a stent with a framework attached to a fabric tube by a plurality of suture ties. The fabric tube includes a plurality of discrete attachment areas that are at least partially surrounded by at least one permeable graft area. The fabric tube is one of a weave and a knit of thermoplastic yarn. Each of the suture ties associated with the discrete attachment areas at least one of penetrates through and encircles a respective one of the discrete attachment areas. The weave or knit of the discrete attachment areas is identical to that of the permeable graft area with an exception that a wall thickness of each of the discrete attachment areas is flattened relative to, and thinner than, a wall thickness of the permeable graft area.

20 Claims, 4 Drawing Sheets

AORTIC STENT GRAFT WITH DURABLE SUTURE ATTACHMENT SITES

TECHNICAL FIELD

The present disclosure relates generally to aortic stent grafts, and more particularly to a fabric tube that has discrete attachment areas for improved attachment durability to a stent framework.

BACKGROUND

Aortic stent grafts typically include a stent with a framework attached to a fabric tube with a plurality of suture ties. Although these medical device implants have seen tremendous success for many years, failures can occur. For instance, rare occurrences of top stent separation in vivo can be a serious problem, and is typified by sutures tearing through the fabric tube due to issues such as uneven load distribution in aortic angulation for aortic abdominal aneurism treatments and other aortic treatments. Co-owned U.S. Pat. No. 7,175,652 seeks to reduce suture tearing by folding the graft material onto itself at the proximal end into a double thickness cuff of the fabric material where suture ties attach the fabric tube to the anchoring portion of the stent. While this strategy is sound, it inherently increases the cross sectional area of the stent graft when in a compressed state, and may incrementally decrease a flow area through a proximal end of the fabric tube.

The present disclosure is directed toward one or more of the problems set forth above.

SUMMARY

An aortic stent graft includes a stent with a framework attached to a fabric tube with a plurality of sutures. The fabric tube includes a plurality of discrete attachment areas that are each at least partially surrounded by a permeable graft area, and the fabric tube is one of a weave or a knit of thermoplastic yarn. Each of the suture ties at least one of penetrates through and encircles a respective one of the discrete attachment areas. The weave or the knit of the discrete attachment areas is identical to that of the permeable graft area with an exception that a wall thickness of each of the discrete attachment areas is flattened relative to, and thinner than, a wall thickness of the permeable graft area.

DETAILED DESCRIPTION

Figure 1:
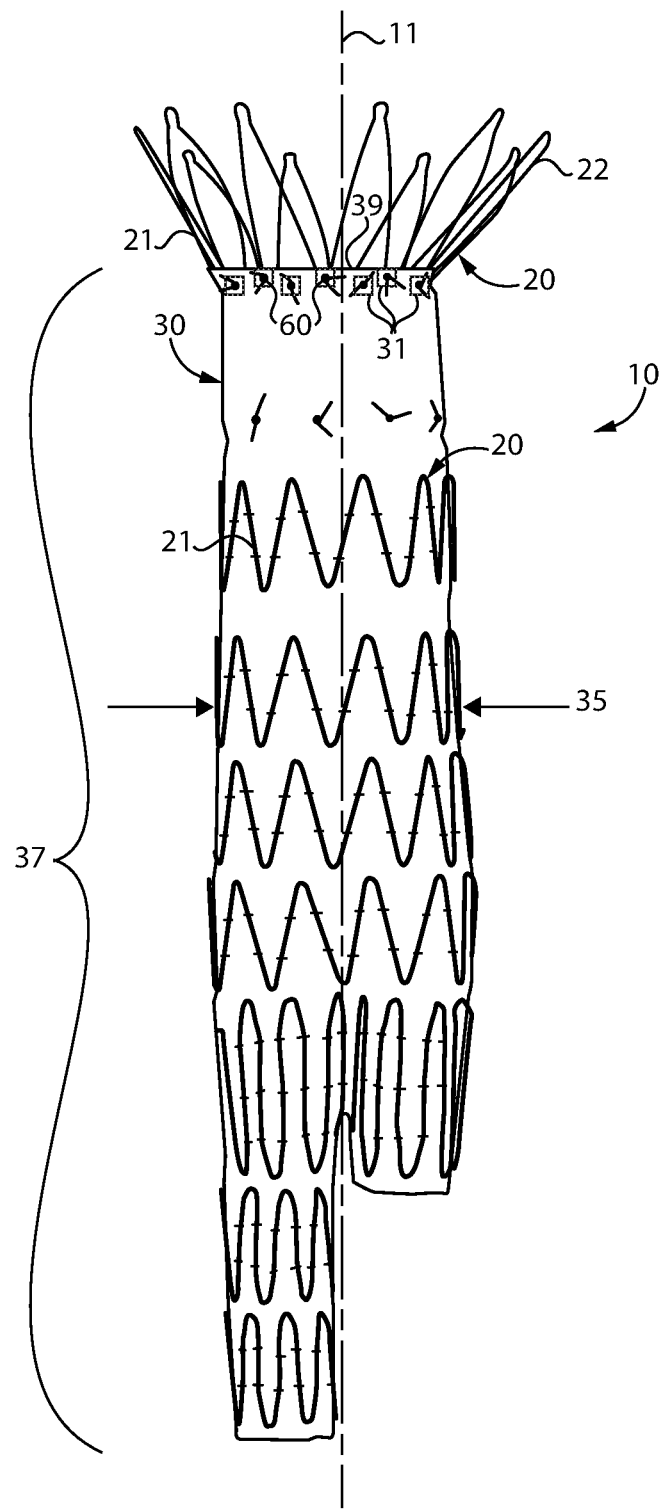
FIG. 1 is a side elevational view of an aortic stent graft according to the present disclosure.

Referring initially to FIG. 1, an aortic stent graft 10 includes a stent 20 that includes a framework 21. Stent graft 10 also includes a fabric tube 30 that is one of a weave or a knit of thermoplastic yarn. As used in this disclosure, thermoplastic yarn may include polyester and may be polyethylene, but not PTFE. The thermoplastic yarn is preferably a multifilament yarn, but could be a monofilament yarn without departing from the present disclosure. The framework 21 of the stent 20 is attached to the fabric tube 30 with a plurality of suture ties 60. Although not necessary, an aortic stent graft 10 according to the present disclosure may include an anchoring portion 22 that like other portions of framework 21 is attached to the fabric tube 30 with suture ties 60. Thus, some or most of the suture tie attachments especially those attaching permeable graft areas to the stent 20, may be identical to the prior art and unaffected by the teachings of the present disclosure. Part of the anchoring portion 22 may be positioned proximal to, and out of contact with, the fabric tube 30 as shown in FIG. 1. Fabric tube 30 may define a central axis 11 and have a length 37. Finally, the aortic stent graft 10 may have an expanded diameter 35 that is sized to bear circumferentially against an aortic wall, with that expanded diameter 35 may be in the range of 12 millimeters to 50 millimeters. Preferably no film or other cover is attached to the fabric tube 30, but a fabric tube with some coating or other covering attached thereto would also fall within the intended scope of the present disclosure. Thus, the fabric tube 30 is an inherent permeable weave or knit, but some non-permeable layer could be attached thereto either covering all or a portion of the fabric tube without departing from the present disclosure. Thus, a non-permeable tube of plastic or some other material would not be considered a fabric tube according to the present disclosure.

Referring now in addition to FIGS. 2-9, various versions of an aortic stent graft according to the present disclosure are illustrated with the same numbers being used to identify identically named features that otherwise have different shapes or attributes in each of the different versions. Although the present disclosure focuses on the attachment of a top stent or anchoring portion 22 attachment to the associated fabric tube 30, the present disclosure could apply to any portion of the stent framework 21 where it attaches to the fabric tube 30 by suture ties 60. In all versions of the present disclosure, the fabric tube 30 includes a plurality of discrete attachment areas 31 that are each at least partially surrounded by at least one permeable graft area 32. Although many of the suture ties 60 that attach different portions of the stent 20 to the fabric tube 30 will be indistinguishable from those associated with the prior art, some of the suture ties 60 at least one of penetrate through and encircle a respective one of the discrete attachment areas 31. The weave 40 or the knit of the discrete attachment areas 31 is identical to the permeable graft area 32 with an exception that a wall thickness 33 of each of the discrete attachment areas 31 is flattened relative to, and thinner than, a wall thickness 34 of the permeable graft area 32.

The change in the discrete attachment areas 31 relative to the permeable graft area 32 may be accomplished by a combination of heat and pressure applied to the discrete attachment areas 31. This may be accomplished before the fabric tube 30 is attached to stent 20, such as by mounting fabric tube 30 on a mandrel and applying heat and pressure to the selected discrete attachment areas 31. However, the heat and pressure may be applied after the stent 20 has been attached to the fabric tube 30 with associated fabric ties 60 without departing from the present disclosure. The heat and pressure applied may cause some melting of the underlying thermoplastic yarns, but not to a level where the structure of the weave 40 or knit is destroyed, but some melt attachment may occur where the thermoplastic yarns would otherwise be in contact. In other words, in the discrete attachment areas 31, warp 42 and weft 43 yarns may have some melted attachment to each other where they were otherwise contact in the normal un-effected areas of the weave structure. Thus, the heated pressure applied in the discrete attachment areas 31 may be sufficient to cause plastic deformation of the weave or knit in those areas relative to the weave or the knit in the permeable graft areas 32. Although not necessary, the discrete attachment areas 31 may be less permeable than the permeable graft areas 32, and make up a minority of the surface area of the overall surface area of fabric tube 30. In the event that the thermoplastic yarn is made up of multi-filament, one might expect, in some versions of the present disclosure, that some of the individual filaments may have melted together.

Figure 2:
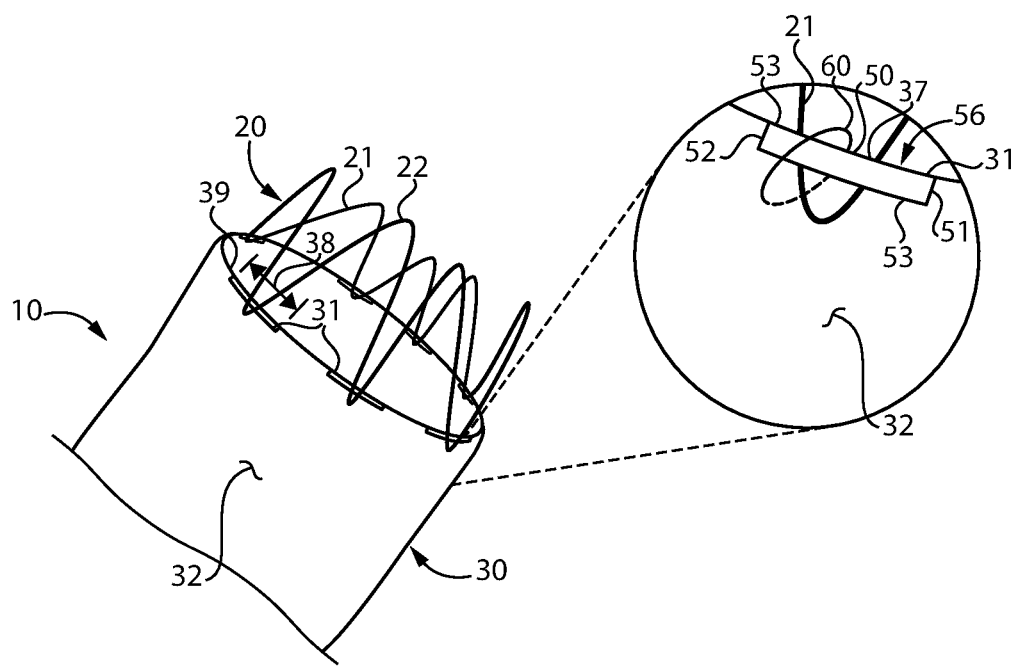
FIG. 2 is a partial perspective and an enlarged view of a proximal end of an aortic stent graft according to the present disclosure.
Figure 3:
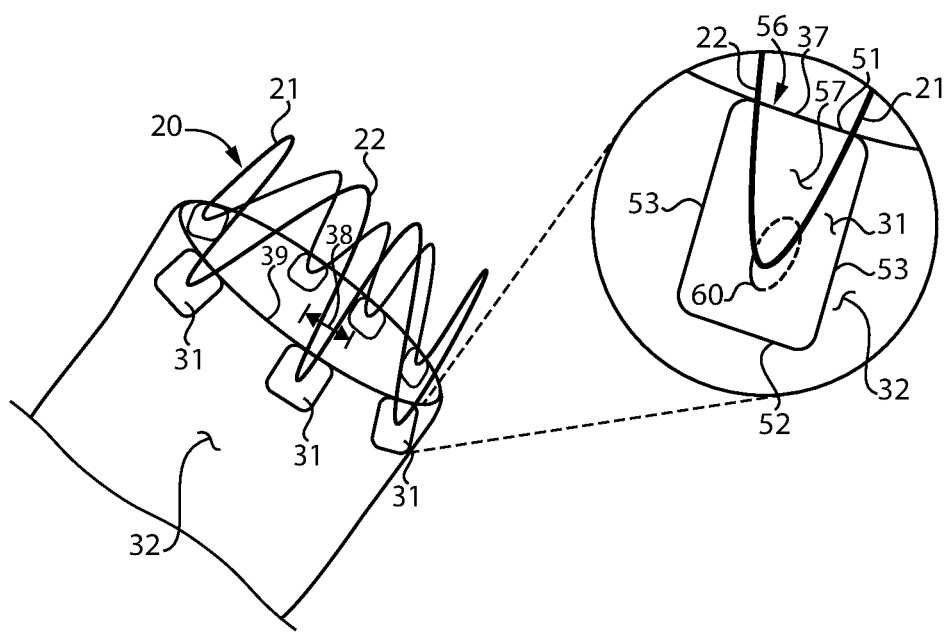
FIG. 3 is a partial perspective and an enlarged view of a proximal end of an aortic stent graft according to another aspect of the present disclosure.

FIG. 2 shows a version in which the fabric tube edge is melted to define individual discrete attachment areas 31. Each include an edge 57 that is a segment 38 of a circumferential end 39 of the fabric tube 30. This may be accomplished by applying heat and pressure to melt the thermoplastic yarns in the discrete attachment area at the proximal end of the fabric tube to create a stronger edge resistance to suture pull through, which is altered with normal graft edge sealing to prevent cracking and enable loading into a sheath for delivery in a conventional manner. In the version of FIG. 2, the individual suture ties 60 encircle the discrete attachment areas 31. Both FIG. 2 and FIG. 3 show discrete attachment areas 31 that each have an elongated shape 50 that may be rectangular 56 and include a first end 51 separated from a second end 52 by elongated sides 53. FIG. 3 shows a versions with larger discrete attachment areas 31 than those associated with FIG. 2 and with heat and pressure applied to merely flatten, may be without melting, the discrete attachment areas 31, which are alternated with unaltered and un-flattened permeable graft areas 32 to facilitate loading of the stent graft 10 into a sheath for delivery to an aorta. Thus, the present disclosure contemplates the application of heat and pressure to merely flatten the weave in the discrete attachment areas 31 with or without associated melting of individual filaments within the thermoplastic yarn and/or melting attachment of individual warp and weft yarns to each other. Thus, when no melting occurs, the warp 42 and weft 43 may have an increased contact area relative to that in the unaffected permeable graft area. In the version of FIG. 3, the suture ties 60 penetrate through the associated discrete attachment area 31 when attaching the underlying or overlaying stent 20 to the fabric tube 30.

Figure 4:
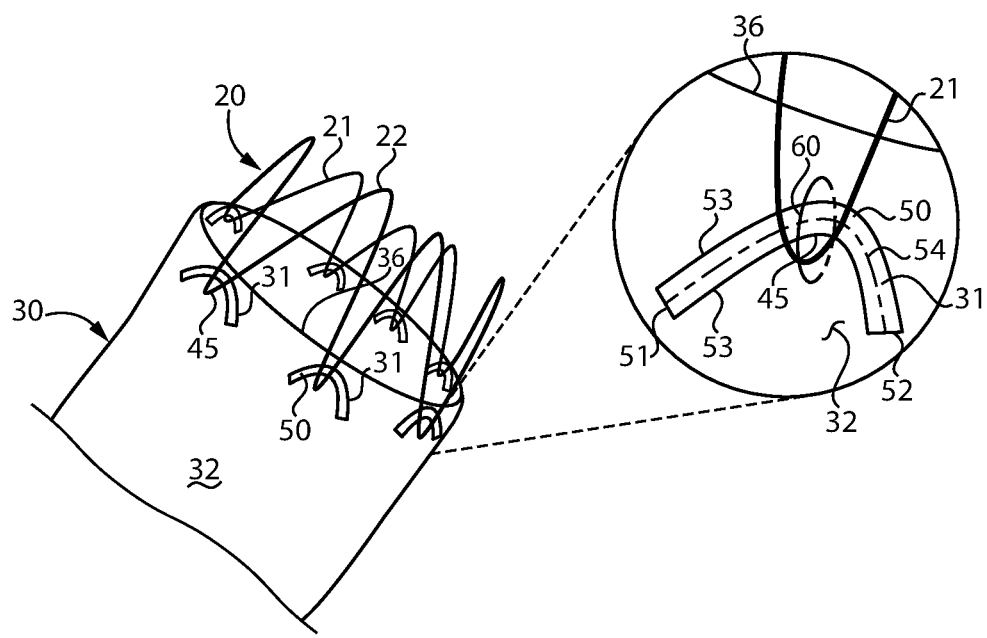
FIG. 4 is a partial perspective and an enlarged view of a proximal end of an aortic stent graft according to still another aspect of the present disclosure.

FIG. 4 shows a version in which the elongated shape 50 of the discrete attachment area 31 may be thought of as including a curved line 54 that intersects the first and second ends 51 and 52, with the curved line 54 being convex relative to a proximal end 36 of the fabric tube 30. Again, the thermoplastic yarn in the discrete attachment area 31 may or may not include melting, but is flattened and has a thinner wall thickness relative to the unaffected and surrounding permeable graft area 32. Furthermore, the curved line 54 may be considered to include a vertex 45 around which the associated suture tie 60 encircles, and the vertex 45 points away from the proximal end 36 of the fabric tube 30. The heated and may be partially melted discrete attachment area 31 of pattern shown in FIG. 4 may serve to reinforce portions of the stent graft 10 that might bear tensile load from sutures 60 and help to prevent pull-through while being alternated with, and may be surrounded by, unaffected or unheated areas associated with the permeable graft areas 32 to facilitate loading in a sheath for delivery.

Figure 5:
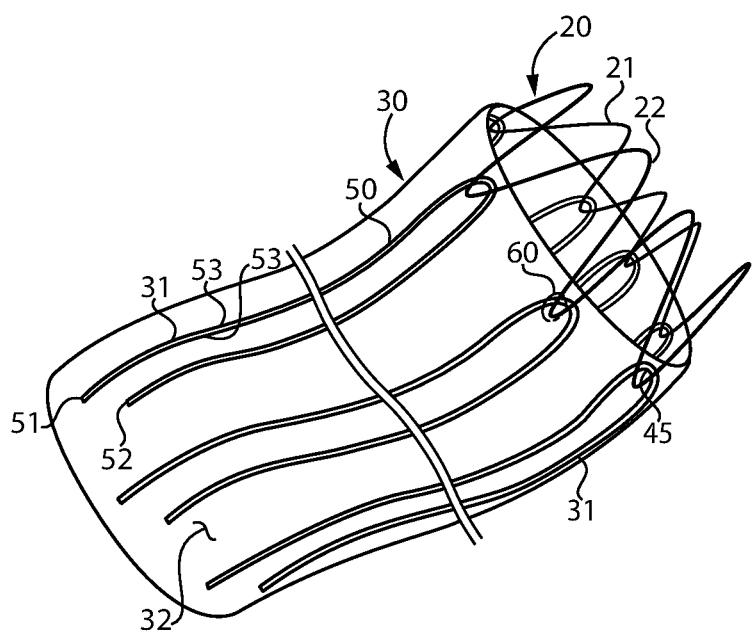
FIG. 5 is a perspective view of an aortic stent graft according to still another aspect of the present disclosure.
Figure 6:
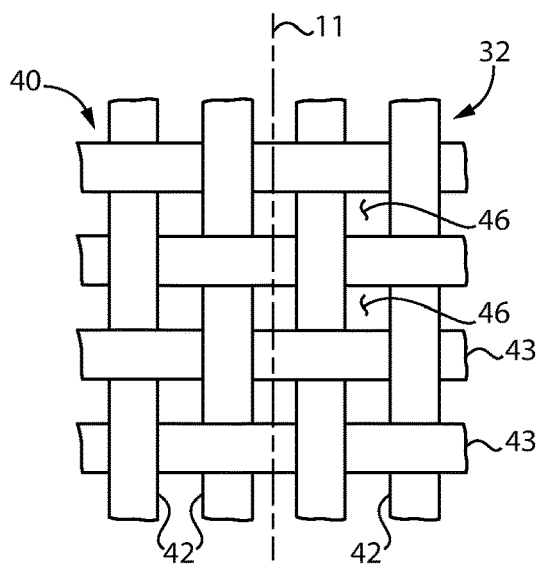
FIG. 6 is a close up view of a weave of a permeable graft area of a fabric tube according to the present disclosure.

The version shown in FIG. 5 is of interest for showing patterns similar to that of FIG. 4 except that the heated or partially melted discrete attachment areas 31 may extend in various patterns and designs may be even a majority of the length 37 of the fabric tube 10 to help harness strength and load resistance from the whole fabric tube 30 into the attachment of the anchoring portion 22 to the fabric tube 30. In both the versions of FIGS. 4 and 5, the respective suture ties 60 encircle the discrete attachment areas 31. However, the suture ties could penetrate through the discrete attachment areas 31 without departing from the present disclosure. The present disclosure also contemplates versions in which the suture ties 60 include a sufficient number of loops to both penetrate through and encircle the individual discrete attachment area 31. The vertex 45 of the discrete attachment area 31 may be separated from the first and second ends 51 and 52 by a distance that is on a same order as a length 37 of the fabric tube 30, as shown in FIG. 5.

Figure 8:
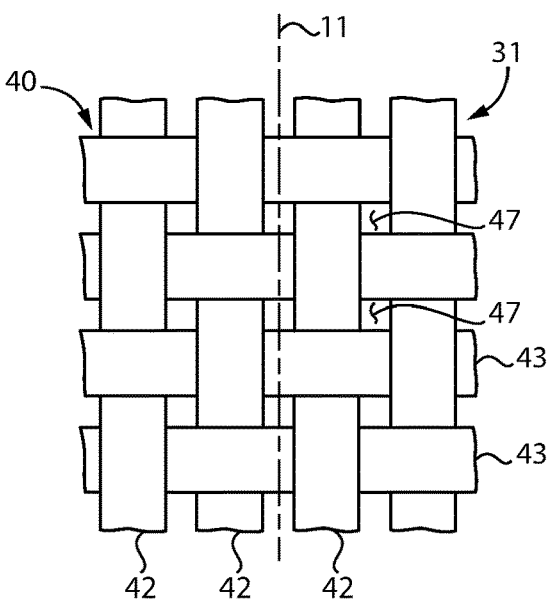
FIG. 8 is a close up view of a weave of a discrete attachment area counterpart to the weave shown in FIGS. 6 and 7.
Figure 7:
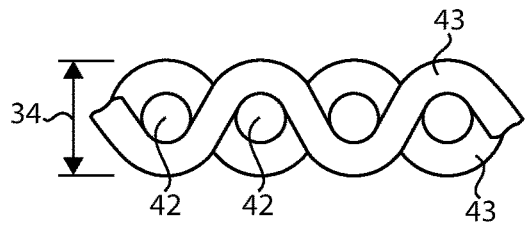
FIG. 7 is a cross sectional view of the weave of FIG. 6.
Figure 9:
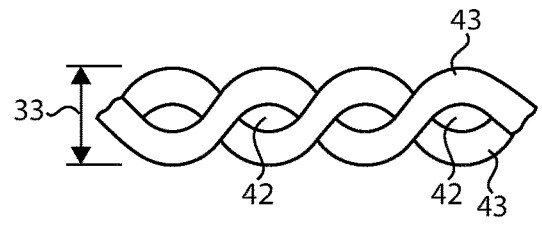
FIG. 9 is a cross sectional view of the discrete attachment area weave shown in FIG. 8.

Referring now specifically to FIGS. 6-9, close up views of a weave associated with the permeable graft area 32 and a counterpart discrete attachment area 31 help illustrate the changes that occur when heat and pressure are applied to the weave 40 in accordance with the present disclosure. In most instances, the warp yarns 42 will be oriented parallel to the axis 11 of the fabric tube, reflecting that the fabric tube 30 may have been formed in a conventional manner on a Jacquard loom as is known in the art. Weft yarns 43 may be oriented perpendicular to the warp yarns 42 in a conventional manner. Although these illustrations show a simple plain weave pattern, other weaving patterns could be utilized without departing from the present disclosure. The warp 42 and weft 43 yarns define openings 46 that render the weave 40 permeable. As best shown in FIG. 8, these associated openings 47 in the discrete attachment area 31 may be made smaller through the application of heat and pressure, but the weave 40 is otherwise identical to that of the associated permeable graft portion 32. However, one could expect that the wall thickness 33 in the discrete attachment area 31 will be both flattened and thinner than the counterpart wall thickness 34 in the permeable graft area 32.

Figure 10:
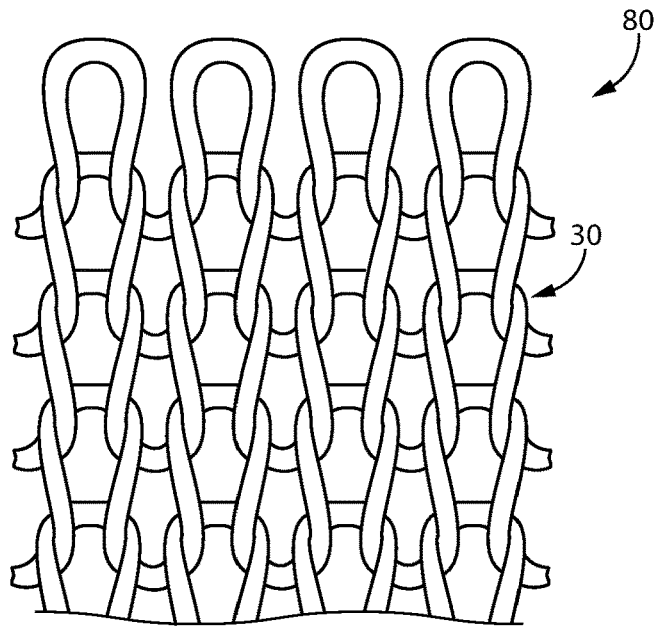
FIG. 10 is a close up view of a knit for a portion of a fabric tube according to another aspect of the present disclosure.

FIG. 10 is of interest for showing an alternative to the weave 40 described earlier. In particular, FIG. 10 shows a portion of a fabric tube 30 made up of a knit 80, which may be considered an alternative to a weave according to the present disclosure.

INDUSTRIAL APPLICABILITY

The present disclosure relates generally to aortic stent grafts. The present disclosure finds specific applicability to aortic stent grafts that include a fabric tube made up of a weave or knit of thermoplastic yarn attached to an overlying and/or underlying framework 21 of a stent 20. Finally, the present disclosure finds specific application in attachment areas of stent grafts that have experienced rare failures, including where an anchoring portion 22 is attached to the stent graft 10 with suture ties 60.

The present disclosure has the advantage that the technique of applying pressure and heat to discrete attachment areas 31 may be applied to existing aortic stent grafts that are otherwise unaltered and have been sold and used for years. In addition, because no added material is added to the aortic stent graft 10 according to the present disclosure, there may be no impact on the packing volume of the aortic stent graft 10 when compressed and housed in a sheath for delivery to an implantation site. Thus, the present disclosure may have no adverse effect on material folding with no added volume because no added material is applied. Since the existing material is being partially modified with heat and pressure, a same sheath size or maybe even perhaps smaller sheath sizes may be employed during the delivery of the associated stent graft 10 according to the present disclosure. One could expect decreased failure outcomes where prior art stent grafts have fabric tubes that tear free of the associated framework 21 due to the additional support and tensile load resistance afforded by the discrete attachment areas 31 according to the present disclosure. A stent graft with added material in an area associated with enhanced attachment is not an aortic stent graft according to this disclosure.

The present description is for illustrative purposes only, and should not be construed to narrow the breadth of the present disclosure in any way. Thus, those skilled in the art will appreciate that various modification might be made to the presently disclosed embodiments without departing from the full and fair scope and spirit of the present disclosure. Other aspects, features and advantages will be apparent upon an examination of the attached drawings and appended claims.

What is claimed is:

1. An aortic stent graft comprising:
a stent that includes a framework; a fabric tube that includes a plurality of discrete attachment areas that are each at least partially surrounded by at least one permeable graft area, and the fabric tube is one of a weave or a knit of thermoplastic yarn;
a plurality of suture ties that attach the framework to the fabric tube, and each of the suture ties penetrates through and/or encircles a respective one of the discrete attachment areas; and
wherein the weave or the knit of the discrete attachment areas is identical to that of the permeable graft area with an exception that a wall thickness of each of the discrete attachment areas is flattened relative to, and thinner than, a wall thickness of the permeable graft area.

2. The aortic stent graft of claim 1 wherein the weave or the knit at the discrete attachment areas are plastically deformed relative to the weave or the knit of the permeable graft area.

3. The aortic stent graft of claim 1 wherein the discrete attachment areas are less permeable than the permeable graft area.

4. The aortic stent graft of claim 1 wherein the framework includes an anchoring portion; and
the anchoring portion is attached to the discrete attachment areas with a portion of the suture ties.

5. The aortic stent graft of claim 4 wherein a part of the anchoring portion is positioned proximal to, and out of contact with, the fabric tube.

6. The aortic stent graft of claim 1 wherein the thermoplastic yarn is a polyester yarn.

7. The aortic stent graft of claim 1 wherein the thermoplastic yarn includes at least one of polyester and/or polyethylene filaments.

8. The aortic stent graft of claim 1 wherein the thermoplastic yarn is a multifilament yarn.

9. The aortic stent graft of claim 1 wherein the fabric tube has an expanded diameter that is sized to bear circumferentially against an aortic wall.

10. The aortic stent graft of claim 9 wherein the expanded diameter is a range from 12 mm to 50 mm.

11. The aortic stent graft of claim 1 wherein the discrete attachment areas include filaments that have melted together.

12. The aortic stent graft of claim 1 wherein the fabric tube is a weave with warp yarns oriented parallel to an axis of the fabric tube.

13. The aortic stent graft of claim 1 wherein the discrete attachment areas have an elongated shape with a first end separated from a second end by elongated sides.

14. The aortic stent graft of claim 13 wherein a respective imaginary line positioned in each of the discrete attachment areas and intersecting the first and second ends is a curved line that is convex relative to a proximal end of the fabric tube.

15. The aortic stent graft of claim 14 wherein the respective line defines a vertex that points away from the proximal end of the fabric tube.

16. The aortic stent graft of claim 15 wherein the vertex is closer, than the first and second ends of the discrete attachment area, to the proximal end of the fabric tube; and
the first and second ends of the discrete attachment area is closer, than the vertex, to a distal end of the fabric tube.

17. The aortic stent graft of claim 1 wherein the discrete attachment areas have a rectangular shape.

18. The aortic stent graft of claim 1 wherein an edge of at least one of the discrete attachment areas is a segment of a circumferential end of the fabric tube.

19. The aortic stent graft of claim 1 wherein a portion of the suture ties each penetrate through a respective one of the discrete attachment areas.

20. The aortic stent graft of claim 1 wherein a portion of the suture ties each encircle a respective one of the discrete attachment areas.

* * * * *